United States Patent [19]

Fleming et al.

[11] 3,957,989
[45] May 18, 1976

[54] ANTIVIRAL COMPOSITIONS CONTAINING BIS-BASIC KETONES OF XANTHENE AND XANTHEN-9-ONE

[75] Inventors: Robert W. Fleming, Ann Arbor, Mich.; Arthur D. Sill, Greenhills; Francis W. Sweet, Cincinnati, both of Ohio

[73] Assignee: Richardson-Merrell Inc., Wilton, Conn.

[22] Filed: Feb. 20, 1973

[21] Appl. No.: 333,768

Related U.S. Application Data

[63] Continuation-in-part of Ser. No. 97,379, Dec. 11, 1970, Pat. No. 3,859,286.

[52] U.S. Cl............................... 424/248; 424/244; 424/251; 424/267; 424/274; 424/278
[51] Int. Cl.².......................................... A01N 9/00
[58] Field of Search ........... 424/250, 248, 267, 274, 424/283

[56] References Cited
UNITED STATES PATENTS
3,767,674   10/1973   Nabih .................................. 260/328

OTHER PUBLICATIONS
Cecil et al., A Textbook of Medicine, 9th Ed., W. B. Saunders Co., Phila., Pa., p. 1., (1958).

*Primary Examiner*—Richard L. Huff
*Attorney, Agent, or Firm*—George W. Rauchfuss, Jr.; Eugene O. Retter

[57] ABSTRACT

Novel bis-basic ketones of xanthene and xanthen-9-one have antiviral activity when administered orally and parenterally. The compounds are represented by the following formula:

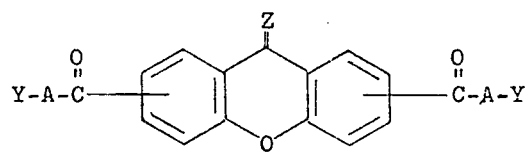

wherein Z is oxygen or $H_2$; each A is a straight or branched alkylene chain having from 1 to about 6 carbon atoms; and each Y is A. the group

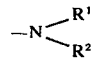

wherein $R^1$ and $R^2$ are individually hydrogen, lower alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group; or B. the group

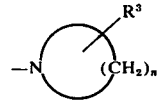

wherein $n$ is a whole integer from 4 to 6, and $R^3$ is hydrogen, lower alkyl of from 1 to about 4 carbon atoms and can be linked to any one of the carbon atoms of the heterocyclic group; or C. the group

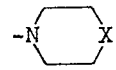

wherein X is oxygen or $NR^4$, and $R^4$ is hydrogen or lower alkyl of from 1 to about 4 carbon atoms;
or a pharmaceutically acceptable acid addition salt thereof.

These compounds can be prepared by several different methods.

28 Claims, No Drawings

ANTIVIRAL COMPOSITIONS CONTAINING BIS-BASIC KETONES OF XANTHENE AND XANTHEN-9-ONE

RELATED APPLICATION

This application is a continuation-in-part of application Ser. No. 97,379, filed Dec. 11, 1970, now U.S. Pat. No. 3,859,286 issued Jan. 7, 1975.

FIELD OF INVENTION

This invention relates to novel bis-basic ketones of xanthene and xanthen-9-one, their method of preparation and use as antiviral agents.

SUMMARY OF INVENTION

The compounds of this invention include both the base form and pharmaceutically acceptable acid addition salts thereof wherein the base form is represented by the formula:

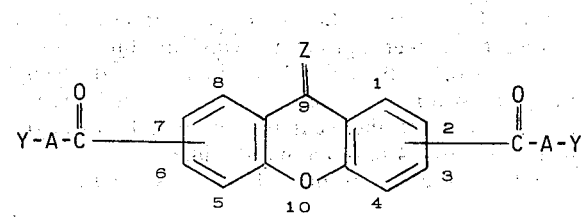

Formula I wherein Z is oxygen or $H_2$; each A is a straight or branched alkylene chain of from 1 to about 6 carbon atoms; and each Y is A. the group

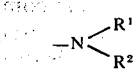

wherein $R^1$ and $R^2$ are individually hydrogen, lower alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group; or B. the group

wherein $n$ is a whole integer of 4 to 6, and $R^3$ is hydrogen, lower alkyl of from 1 to about 4 carbon atoms and can be linked to any one of the carbon atoms of the heterocyclic group; or C. the group

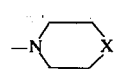

wherein X is oxygen or $NR^4$, and $R^4$ is hydrogen or lower alkyl of from 1 to about 4 carbon atoms.

DETAILED DESCRIPTION OF INVENTION

The compounds of this invention are xanthenes when Z represents $H_2$ and xanthen-9-ones when Z represents oxygen as indicated by the following Formulas II and III, respectively, wherein A and Y have the meanings given hereinbefore:

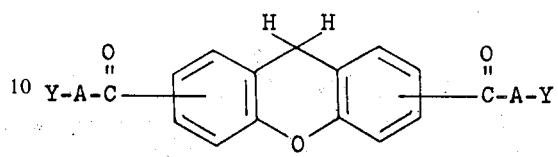

Formula II

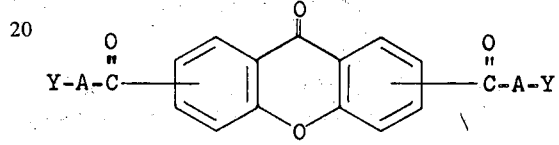

Formula III

The basic ketone group, that is,

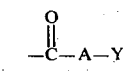

of Formula I can be linked to the tricyclic ring system of xanthene and xanthen-9-one by replacement of any one of the four hydrogens of the benzenoid ring to which such group is attached. Thus, one of the groups will be in any of the positions of 1 through 4 of the tricyclic ring system, and the other will be in any of the positions 5 through 8. Preferably, one of the basic ketone groups is in the 2-position and the other in the 7-position of the tricyclic ring system.

It is apparent from Formula I and its description that compounds can have structures wherein Y is the group

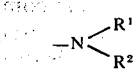

as more fully shown by the following Formula IV, or wherein Y is the group

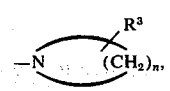

as more fully shown by the following Formula V, or wherein Y is the group

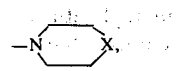

as more fully shown by the following Formula VI below:

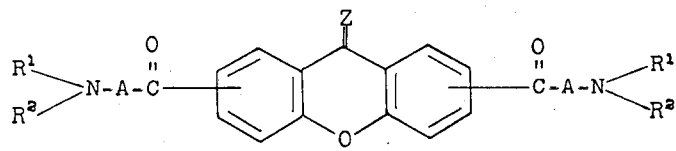 Formula IV

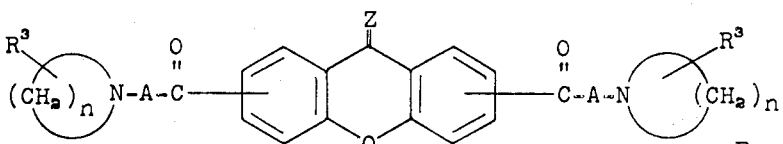 Formula V

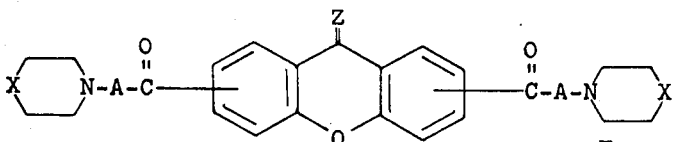 Formula VI

In the Formulas IV, V and VI, the various symbols, Z, A, $R^1$, $R^2$, $R^3$, X and n have the meanings specified hereinbefore.

Each of the symbols A in the compounds of the above Formulas IV, V and VI is an alkylene group having from 1 to about 6 carbon atoms which can be a straight chain, that is, for example, $-CH_2-(CH_2)_m-$ wherein m is a whole integer from 0 to 5, or a branched chain. Each of the alkylene groups as represented by A can be the same or different. Preferably these groups are the same. Illustrative of alkylene groups as represented by A there can be mentioned for example, methylene, 1,2-ethylene, 1,3-propylene, 1,4-butylene, 1,5-pentylene, 1,6-hexylene, 2-methyl-1,4-butylene, 2-ethyl-1,4-butylene, 3-methyl-1,5-pentylene and the like.

Each amino group of the compounds of Formula IV, that is,

can be a primary, a secondary or a tertiary amino group. Each $R^1$ and $R^2$ is individually hydrogen, lower alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group. Preferably each of the amino groups as represented by

is a tertiary amino group.

The term lower akyl as used in reference to the compounds of Formula IV relates to straight or branched alkyl chains having from 1 to about 6 carbon atoms. Illustrative of lower alkyls as can be represented by each $R^1$ or $R^2$ in the compounds of Formula IV there can be mentioned, for example, methyl, ethyl, n-propyl, isopropyl, n-butyl, secondary-butyl, n-amyl, iso-amyl, n-hexyl and the like.

Illustrative of cycloalkyl groups as represented by each $R^1$ and $R^2$ in the compounds of Formula IV there can be mentioned, for example, cyclopropyl, cyclobutyl, cyclopentyl, and cyclohexyl.

When $R^1$ or $R^2$ in the compounds of Formula IV represents an alkenyl group, the vinyl unsaturation is in a position other than the 1- position of said alkenyl group. Illustrative of alkenyl groups as can be represented by $R^1$ or $R^2$ there can be mentiond, for example, allyl, 3-butenyl, 4-hexenyl and the like.

Each heterocyclic group of Formula V, that is,

can be a monocyclic heterocyclic group such as those generally equivalent to di(lower)alkylamino groups in the pharmaceutical arts or substituted monocyclic heterocyclic groups. The heterocyclic groups in the compounds of Formula V can be 5-, 6- or 7-membered rings, that is, n is 4, 5 or 6. The $R^3$ group can be hydrogen or a straight or branched lower alkyl chain of from 1 to about 4 carbon atoms. Illustrative of heterocyclic groups as represented by each

there can be mentioned, for example, piperidino, pyrrolidino, 4-methylpiperidino, 3-methylpiperidino, 4-tert-butylpiperidino or the like.

The heterocyclic group of Formula VI, that is,

in addition to the one nitrogen atom, contains a second hetero atom, that is, X is oxygen or $NR^4$. The $R^4$ group can be hydrogen or a straight or branched lower alkyl chain of from 1 to about 4 carbon atoms. As examples of heterocyclic groups as represented by

there can be mentioned, for example, morpholino, piperazino, N-(lower)alkylpiperazino, such as, for example, N-methyl- or N-ethylpiperazino and the like.

Illustrative of base compounds of this inention as represented by Formula I there can be mentiond 2,7-bis(dimethylaminoacetyl)xanthene, 2,7-bis(diethylaminoacetyl)xanthene, 2,7-bis[2-(N-methylcyclohexylamino)acetyl]xanthene, 2,7-bis-(piperidinoacetyl)xanthene, 2,7-bis(morpholinoacetyl)xanthene, 2,7-bis(3-diethylaminopropionyl)xanthene, 2,6-bis(diethylaminoacetyl)xanthene, 2,7-bis(4-diethylaminobutyryl)xanthene, 2,7-bis(4-piperidinobutyryl)xanthene, 2,7-bis(4-morpholinobutyryl)xanthene, 3,6-bis(3-piperidinopropionyl)xanthene, 2,7-bis(5-dimethylaminovaleryl)xanthene, 2,7-bis(5-piperidinovaleryl)xanthene, 2,7-bis(5-diallylaminovaleryl)xanthene, 2,6-bis[4-(N-methylpiperazino)butyryl]xanthene, 2,7-bis(dimethylaminoacetyl)xanthen-9-one, 2,7-bis(4-piperidinobutyryl)-xanthen-9-one, 2,7-bis(5-piperidinovaleryl)xanthen-9-one, 3,6-bis[2-(4-propylpiperidino)acetyl]xanthen-9-one and the like.

Pharmaceutically acceptable acid addition salts of the base compounds of this invention are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric citric, ascorbic, maleic, hydroxymaleic, benzoic, hydroxybenzoic, phenylacetic, cinnamic, salicylic, 2-phenoxybenzoic and the like, or sulfonic acids such as methane sulfonic, 2-hydroxyethane sulfonic acid and the like. Mono- or di-acid salts may be formed, and the salts can be hydrated or substantially anhydrous.

It has been found that the compounds of this invention are effective for inactivating or inhibiting a broad variety of viruses and can thus be employed as antiviral agents. These compounds are effective for preventing or inhibiting characteristic viral disease symptoms in a host by a wide variety of methods of application and composition. They can be administered for an antiviral effect by means which subject the host, or such host and a virus, to the active inredients. The host is subjected to the active ingredients by bringing together an active ingredient and host, for example, by applying or contacting the host with such active ingredient or simply administering the active ingredient to the host. This includes subjecting the host to such active inredient prior to infection with a virus, that is, prophylactic use, as well as subjecting the host to such active ingredient after infection, that is, therapeutic use. Thus, in viable biological material hosts subjected to the active inredients, the replication of viruses is inhbitied when the host is infected before or after being subjected to such ingredients. Also, administration by various routes of the active ingredients to an animal host prior to or after infection with the virus prevents or inhibits viral replication and the development of the various disease conditions characteristic of the particular virus. By the term "infection" we simply mean invasion of the host with a pathogenic virus. By the term "host" we mean viable biological material or intact animals which are capable of inducing the formation of interferon and which can support the replication of a virus. Preferably the host is of animal and particularly warm blooded or mammalian origin. Illustrative of hosts for various viruses there can be mentioned viable biological material such as can be used in the production of vaccines, for example, tissue cultures such as that of kidney, lung, amnion cells, embryos, for example, chick allantoic fluid; and various animals, for example, warm blooded animals such as birds or mammals, including mice, rats, guinea pigs, gerbils, ferrets and the like.

The mode of activity of the active ingredients is not rigourously defined. Inter alia, the active inredients induce the formation of interferon when a host is subjected to such ingredients. Interferon is a known antiviral substance which is involved with the inhibition of the replication of viruses in the presence of a host cell. Some of the viruses susceptible to replication inhibition by inerferon are set forth in Horsfall and Tamm, "Viral and Rickettsial Infections of Man", 4th Edition (1965), J. B. Lippencott Company, pages 328–329.

The compounds of the present invention can be administered to animals such as warm blooded animals and particularly mammals. to prevent or inhibit infections of picornavirus, for example, encephalomyocarditis; myxovirus, for example, Influenze $A_2$ (Jap/305); arbovirus, for example, Semliki forest; Herpes virus group, for example, herpes simplex; and poxviruses; for example, Vaccinia IHD. When administered prior to infection, that is, prophylactically, it is preferred that the administration be within 0 to 96 hours prior to infection of the animal with pathogenic virus. When administered therapeutically to inhibit an infection, it is peferred that the administration be within about a day or two after infection with pathogenic virus.

The dosage administered will be dependent upon the virus for which treatment or prophylaxis is desired, the type of animal involved, its age, health, weight, extent of infection, kind of concurrent treatment, if any, frequency of treatment and the nature of the effect desired. Illustratively, a daily dosage of the active ingredients will generally range from less than about 0.1 to over about 500 mg (milligram) per kg (kilogram) of body weight. Illustratively, dosage levels of the administered active ingredient can be intravenous 0.1 to about 10 mg/kg; intraperitoneal, 0.1 to about 50 mg/kg; subcutaneous, 0.1 to about 250 mg/kg; oral, 0.1 to about 500 mg/kg and preferably about 1 to about 250 mg/kg; intranasal instillation, 0.1 to about 10 mg/kg; and aerosol, 0.1 to about 10 mg/kg of animal body weight.

The novel compounds, together with conventional pharmaceutical carriers can be employed in unit dosage forms such as solids, for example, tablets or capsules or liquid solutions, suspensions or elixirs for oral administration and injections, or liquid solutions, suspensions, emulsions and the like for parenteral use. The quantity of active ingredient in each dosage will generally differ depending on the type of unit dosage, the type of animal and its weight. Thus, each dosage can contain from less than about 2.0 mg to over 3 grams of active inredients in a significant quantity of a non-toxic pharmaceutical carrier of the type that can be taken orally, applied topicaly, bucally or parenterally.

The pharmaceutical carrier can, as previously indicated, be a sterile liquid such as water and oils, with or without the addition of a surfactant. Illustrative of oils there can be mentioned those of petroleum, animal, vegetable or synthetic origin, for example, peanut oil, soybean oil, mineral oil, sesame oil, and the like. In general, water, saline, aqueous dextrose, and related sugar solutions and glycols such as propylene glycol or polyethylene glycol are preferred liquid carriers, particularly for injectable solutions. Sterile injectable solutions such as saline, for example, isotonic saline, will ordinarily contain from about 0.5% to 25% and preferably from about 1 to 10% by weight of the active ingredient in the composition.

As mentioned above, oral administration can be in a suitable suspension or syrup, in which the active ingredient ordinarily will constitute from about 0.5 to 10%, and preferably from about 1% to 5%, by weight. The pharmaceutical carrier in such composition can be a watery vehicle such as an aromatic water, a syrup or a pharmaceutical mucilage; also, a suspending agent for viscosity control such as magnesium aluminum silicate, carboxymethylcellulose or the like as well as a buffer, preservative, etc.

The active ingredients can also be admixed in animal feed or incorporated into the animal's drinking water. For most purposes, an amount of active ingredient will be used to provide from about 0.0001% to 0.1% by weight of the active ingredient based on the total weight of feed intake. Preferably, from 0.001% to 0.02% by weight will be used. The selection of the particular feed is within the knowledge of the art and will depend, of course, on the animal, the economics, natural materials available, and the nature of the effect desired.

The active ingredients can be admixed in animal feed concentrates, suitable for preparation and sale to farmers or livestock growers for addition to the animal's feedstuffs in appropriate proportion. These concentrates can ordinarily comprise about 0.5% to about 95% by weight of the active ingredient compounded together with a finely divided solid, preferably flours, such as wheat, corn, soya bean and cottonseed. Depending on the recipient animal, the solid adjuvant can be ground cereal, charcoal, fuller's earth, oyster shell and the like. Finely divided attapulgite and bentonite can also be used.

The feed compositions, as well as the feed concentrates, can additionally contain other components of feed concentrates or animal feeds, as will be readily understood. Other particularly important additives include proteins, carbohydrates, fats, vitamins, minerals, antibiotics, etc.

For use as aerosols the active ingredients can be packaged in a pressurized aerosol container together with a gaseous or liquefied propellant, for example, dichlorodifluoromethane, carbon dioxide, nitrogen, propane, etc. with the usual adjuvants such as co-solvents, and wetting agents, as may be necessary or desirable.

Typical surface active agents (Kirk and Othmer, *Encyclopedia of Chemical Terminology*, 1954, Vol. 13, page 513), particularly emulsifying and dispersing agents which can be used in the compositions of this invention are, for example, fatty alcohol sulfates such as sodium lauryl sulfate, aliphatic or aromatic sulfonates, such as sulfonated castor oil, and nonionic types of emulsifying or dispersing agents such as the high molecular weight alkyl polyglycol ethers, such as dodecyl polyglycol ethers containing from about 25 to 75 carbon atoms.

A desirable mode of administration for the compounds (active ingredients) of this invention is particularly, such as by normally liquid injectable compositions, for example, for intramuscular or subcutaneous administration. In such compositions the quantity of active ingredient can vary from about 0.05% to 20% by weight of the composition and preferably from about 0.1% to 10% by weight. In order to minimize or eliminate irritation at the site of injection, the parenteral compositions can contain a non-ionic surfactant such as those having an HLB (hydrophile-lipophile balance) of about 12 to 17. Such formulations can be solutions, suspensions or emulsions in conventional liquid pharmaceutical carriers, for example, sterile liquids such as water, saline, and aqueous dextrose (glucose) and related sugar solutions. The quantity of surfactant in the formulation can vary from about 5% to 15% by weight of the formulation. The quantity of a compound of this invention, either in the base form or a pharmaceutically acceptable acid addition salt in such formulations, can vary over a broad range, such as that mentioned hereinbefore, that is, 0.05% to 20% by weight of the formulation. Preferably, the active ingredient is in the base form. The remaining component or components of such formulations can be a normally active pharmaceutical carrier, for example, isotonic aqueous saline, either alone or together with conventional excipients for injectable compositions. The surfactant can be a single surfactant having the above-indicated HLB or a mixture of two or more surfactants wherein such mixture has the indicated HLB. The following surfactants are illustrative of those which can be used in such formulations. (A) Polyoxyethylene derivatives of sorbitan fatty acid esters, such as the TWEEN series of surfactants, for example, TWEEN 80, and the like. The TWEENS are manufactured by Atlas Powder Company. (B) High molecular weight adducts of ethylene oxide with a hydrophobic base formed by the condensation of propylene oxide with propylene glycol, for example, PLURONIC F-68 which is manufactured by Wyandotte Chemical Company. The preferred surfactant is Polysorbate 80, U.S.P., a polyoxyethylene sorbitan monooleate.

One of the methods used to prepare the compounds of this invention is illustrated by the following reaction scheme:

Reaction 1

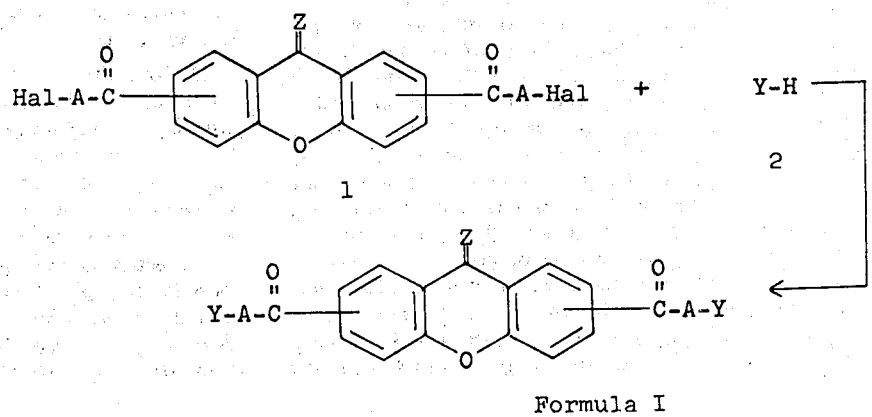

Formula I

In the above reaction Z, A and Y have the meanings defined hereinbefore, and each Hal is either chlorine, bromine or iodine.

The bis-(ω-haloalkanoyl)xanthene derivatives, 1, in which the position of substitution is 2,7-, and $Z = H_2$ can be prepared by a Friedel-Crafts acylation of xanthene. Of suitable acylating agents which may be used there can be mentioned, for example, chloroacetyl chloride, bromoacetyl bromide, 3-chloropropionyl chloride, 4-chlorobutyryl chloride, 5-chlorovaleryl chloride, 5-chloro-4-methylvaleryl chloride, 5-chloro-3-methylvaleryl chloride and the like.

It is apparent that the acylation reaction may be carried out in a variety of solvents and under catalysts of a variety of Lewis acids. The temperature and duration of the reaction may be varied to allow for optimum reaction conditions. A preferred procedure is to combine one equivalent of xanthene with 2.5 equivalents of an acylating agent in methylene chloride followed by portionwise addition of aluminum chloride. The temperature of the reaction is maintained below zero degrees with continuous stirring. After the additions are complete the temperature may be elevated to 25°–40°C. for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic hydrocarbon and Lewis acid. The more reactive halogen derivative, that is, the bis-(ω-iodoalkanoyl)xanthene may be prepared from the corresponding bis-chloro derivative using a halogen exchange reaction under the conditions generally employed in the Conant-Finkelstein reaction.

Of typical amines, 2, useful in Reaction 1 there can be mentioned, for example, ammonia, or a compound which is a potential source of ammonia such as, for example, hexamethylenetetramine and the like; primary amines such as ethylamine, propylamine and the like; and secondary amines such as diethylamine, dibutylamine, piperidine, 4-methylpiperidine, morpholine, piperazine, N-ethylpiperazine, and the like.

The amination of bis(ω-haloalkanoyl)xanthenes, 1, may be carried out under a variety of conditions. For example, compound 1 may be heated together with a large excess of the amine, 2, the excess amine serving as the reaction medium and the hydrohalide acceptor. This method is particularly suitable for readily available amines, the excess of which can be easily removed from the reaction mixture by, for example, distillation at reduced pressure or by washing the product with water. Or, one equivalent of compound 1 and four equivalents of the amine, 2, may be heated together in one of a number of different types of solvents, for example, in aromatic solvents such as benzene, toluene, xylene, and the like; or ethers such as tetrahydrofuran, dioxane and the like; or ketones such as acetone, butanone and the like; or aprotic solvents such as N,N-dimethylformamide, N,N-dimethylacetamide, dimethylsulfoxide and the like; or mixtures of these solvents with water. The reaction between compound 1 wherein the halogen is chlorine and the amine, 2, is frequently promoted by the addition of either sodium or potassium iodide, the iodide being used in either catalytic or stoichiometric amounts. In some cases, it may be advantageous to use only two equivalents of the amine, 2, for each equivalent of the bis(ω-haloalkanoyl)-xanthene, 1, an excess of an inorganic base such as powdered sodium or potassium carbonate being used as the hydrohalide acceptor. The reaction will proceed normally in 12 hours to two weeks at temperatures of −30° to 150°C. As volatile amines are employed, the reaction is best carried out under pressure in a suitable pressure reactor or autoclave.

Alternately, the amination reaction may be carried out on a derivative of compound 1 such as the xanthene or xanthen9-one ketal derivatives, which may be prepared by allowing bis-ω-haloalkanoyl-xanthene or xanthen-9-one derivative and an excess of ethyl orthoformate to react in the presence of an acid catalyst such as hydrochloric acid for several days in a polar solvent such as ethanol, tetrahydrofuran and the like. The aminoketal derivative is hydrolyzed to the product of the invention by warming with dilute acid.

The compounds of Formula I wherein A is an alkylene chain of 3 to 6 carbon atoms and Z is $H_2$ may also be prepared by the reaction of a Grignard reagent with a bis-ester or bis-amide of xanthene as represented by the following reaction:

Reaction 2

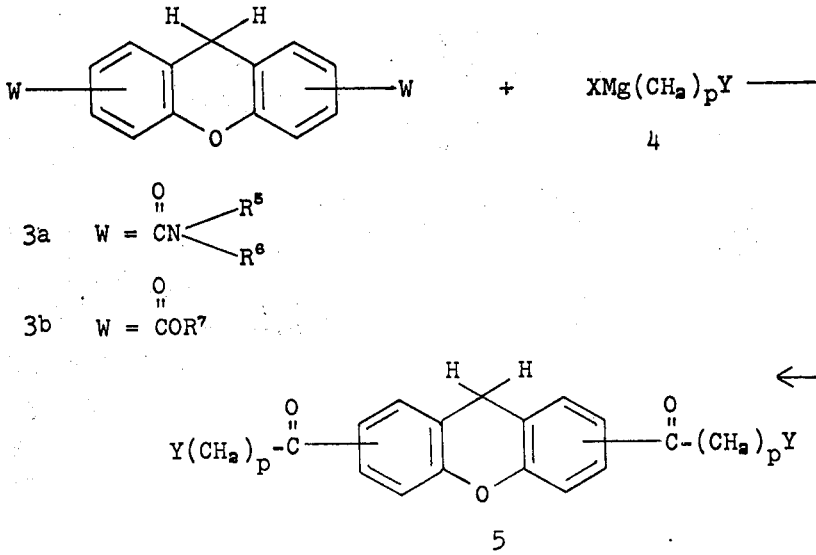

In the above reaction $R^5$ and $R^6$ are hydrogen or lower alkyl, or $-NR^5R^6$ taken together form a saturated monocyclic heterocyclic group such as piperidino or pyrrolidino; $R^7$ may be a straight or branched lower alkyl chain, or an aryl group such as phenyl, benzyl and the like; X is bromine or chlorine, P is an integer of from 3 to 6 and Y may be any of the groups defined hereinbefore except those which contain a hydrogen attached to the nitrogen atom.

The addition of the Grignard reagent, 4, is carried out at low temperatures ranging from $-70°$ to $0°C$. Once this addition is complete, Reaction 2 will proceed in from 1 to 24 hours at a temperature ranging from $0°$ to $80°C$.

The Grignard reagent, 4, may be prepared by reacting magnesium and an aminoalkyl halide of the formula $$X(CH_2)_pY$$

wherein X, $p$ and Y have the meaning defined hereinabove.

The xanthene bis-amides and bis-esters, 3a and 3b, may be prepared by generally known methods from the corresponding xanthene bis-acids. These may be obtained among other procedures by reduction of the corresponding xanthen-9-one bis-acids by known methods such as the Wolff-Kishner reduction or by reduction with sodium and alcohol. The xanthen-9-one bis-acids may be prepared by oxidation of the corresponding dimethylxanthenes [T. Sengoku, J. Pharm. Soc. Japan 53, 962 (1933); M. Schopff, Ber. 25, 3647 (1892) ], by oxidation of higher fused ring analogs [O. Kruber, Ber. 74B, 1688 (1941)] or by the generally known oxidation of a corresponding diacetyl derivative with hypochlorite and the like.

The compounds of Formula I wherein A is $-CH_2CH_2-$ and Y is any of the groups defined hereinbefore, except those which contain two hydrogens on the nitrogen atom, may also be prepared by the Mannich reaction as represented by the following:

By combining one equivalent of compound 6 and two or more equivalents of compound 2 with three or more equivalents of formaldehyde, 7, the reaction will proceed in from 1 to 24 hours in solvents such as water, acetic acid, ethanol, butanol, dioxane, tetrahydrofuran and the like and at temperatures equivalent to the reflux temperature of the solvent. In this reaction either of two sources of formaldehyde may be employed. When formalin is used the reaction may be conducted with a suspension of compound 6 or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehyde either during the reaction or at the end of the reaction.

The secondary amine, compound 2, employed in this reaction may be added to the reaction medium as the hydrochloride salt or as the base form with subsequent in situ formation of the hydrochloride salt by the addition of hydrochloric acid. Of typical secondary amines which may be utilized in the above reaction there can be mentioned, for example, dimethylamine, dibutylamine, piperidine, 4-methylpiperidine, morpholine, N-ethylpiperazine and the like.

The diacetyl xanthene compound, 6, may be prepared by a Friedel-Crafts acylation reaction on xanthene or by a Grignard reaction of a xanthene bis-amide, 3a, or a xanthene bis-ester, 3b, with methylmagnesium halide. The xanthene bis-amides and bis-esters may be obtained by methods described hereinbefore.

Other compounds of Formula I wherein Z is oxygen may be prepared by oxidation of the corresponding xanthene bis-basic ketone compounds, as illustrated in the following reaction:

Reaction 3

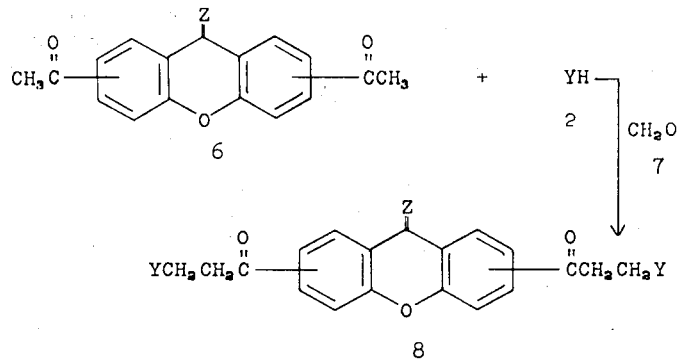

Reaction 4

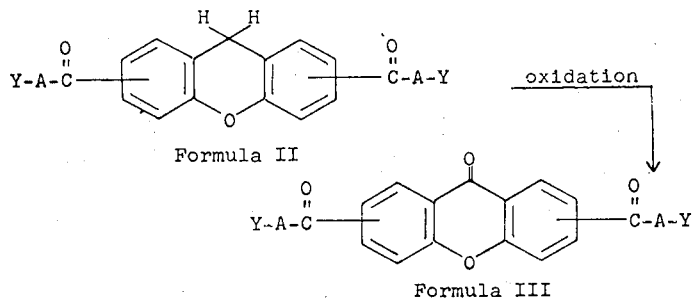

The above oxidation reaction may be carried out using dichromate anion such as sodium dichromate or potassium dichromate as the oxidizing agent. The reaction will proceed in from 15 minutes to 6 hours at a temperature of from 80° to 120°C. The amount of oxidizing agent is limited to the stoichiometric quantity required for oxidation of the 9-methylene group of the xanthene derivative. Suitable solvents for this conversion are, for example, water, acetic acid, tert-butyl alcohol, and the like, or combinations of these solvents. For example, by combining three moles of the xanthene derivative, Formula II, dissolved in acetic acid with four moles of sodium dichromate and refluxing the mixture for 1 to 3 hours, the corresponding xanthen-9-one derivative, Formula III, can be obtained.

Compounds of Formula I wherein Y is —NH$_2$, Z = H$_2$, and A is a straight or branched alkylene chain having from 2 to 6 carbon atoms can be prepared by the following reaction:

Reaction 5

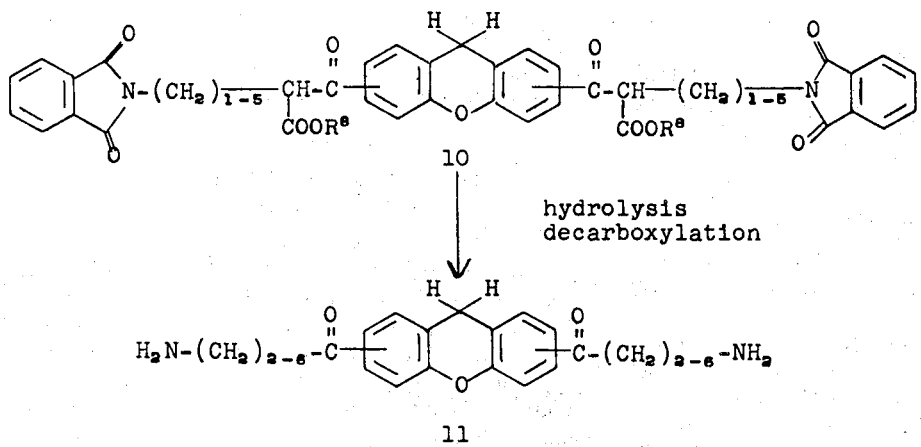

In the above reaction R$^8$ is a lower alkyl. Hydrolysis and decarboxylation of the bis-phthalimido derivative, compound 10, can be carried out in solvents such as water, or lower alcohols such as ethanol, n-butanol and the like in the presence of acetic acid or mineral acids such as hydrochloric acid, sulfuric acid and the like, or mixtures of these acids. The reaction will proceed in from 5 minutes to 48 hours at temperatures equivalent to the reflux temperature of the solvent.

The bis-phthalimido derivative, compound 10, may be prepared by an ester condensation [J. Shivers et al., J. Am. Chem. Soc. 69, 119 (1947)] of a phthalimidoalkyl ester with a xanthene bis-lower alkyl ester, the preparation of which has been described hereinbefore.

Oxidation by procedures described hereinbefore of compound 10 to the corresponding xanthenone derivative followed by hydrolysis and decarboxylation as described above will yield compounds of Formula I where Z is oxygen, Y is NH$_2$ and n is 2-6.

EXAMPLES

Representative compounds of the present invention and several of the methods of preparing them, mentioned above, are illustrated in the following specific examples.

EXAMPLE 1

2,7-BIS(4-CHLOROBUTYRYL)XANTHENE

To a mixture of 91.1 g (0.5 mole) xanthene, 176.3 g (1.25 moles) of 4-chlorobutyryl chloride and 3 liters of dried methylene chloride cooled to -20°C. was added slowly over ½ hour 146.7 g (1.1 moles) of aluminum chloride, maintaining a temperature below −10°C. The reaction mixture was allowed to warm slowly to room temperature and then refluxed for 4 hours and cooled to room temperature. The mixture was decomposed by pouring cautiously into 2 liters of ice water, and the layers were separated. The aqueous layer was extracted again with methylene chloride. The methylene chloride layers were combined and evaporated to a small volume and cooled. The resulting solid was filtered off and recrystallized from acetone to give the desired product. M.P. 131°–132°C.

EXAMPLE 2

2,7-BIS(3-CHLOROPROPIONYL)XANTHENE

Following the procedure of Example 1, only substituting for 4-chlorobutyryl chloride, 158.5 g (1.25 moles) of 3-chloropropionyl chloride, the solid obtained was recrystallized from butanone to yield the desired product. M.P. 180.5°–181°C.

EXAMPLE 3

2,7-BIS(2-CHLOROACETYL)XANTHENE

Following the procedure of Example 1, only substituting for 4-chlorobutyryl chloride, 141.2 g (1.25 moles) of 2-chloro-acetyl chloride, the solid obtained was recrystallized twice from acetone to yield the desired product. M.P. 200°–201°C.

EXAMPLE 4

2,7-BIS(5-CHLOROVALERYL)XANTHENE

Following the procedure of Example 1, only substituting for 4-chlorobutyryl chloride, 194 g (1.25 moles)

of 5-chlorovaleryl chloride, the desired product was obtained. M.P. 134°–135°C.

EXAMPLE 5

2,7-BIS(4-CHLORO-1,1-DIETHOXYBUTYL)XANTHENE

A mixture of 31.3 g (0.08 mole) of 2,7-bis(4-chlorobutyryl)xanthene, 32.6 g (0.22 mole) of triethyl orthoformate, 300 ml. of dried absolute ethanol and 5 ml. of ethanolic HCl was stirred for 24 hours in a stoppered flask. The reaction mixture was decomposed with sodium methoxide. The solution was filtered and the filtrate was evaporated under vacuum to dryness to give the desired product which was isolated as an oily residue.

EXAMPLE 6

2,7-BIS(3-CHLORO-1,1-DIETHOXYPROPYL)XANTHENE

A mixture of 20 g (0.055 mole) 2,7-bis(3-chloropropionyl)-xanthene, 20 g (0.135 mole) of triethylorthoformate, 5 ml. of ethereal HCl, and 400 ml. of tetrahydrofuran was stirred for 6 days in a stoppered flask. The reaction mixture was decomposed with sodium ethoxide in ethanol. The solution was filtered and the filtrate was evaporated under vacuum to dryness to give the desired product which was isolated as an oily residue.

EXAMPLE 7

2,7-DIACETYLXANTHEN-9-ONE

To a solution of 133.1 g (0.5 mole) of 2,7-diacetylxanthene in three liters of glacial acetic acid was added slowly over 1½ hours 149.0 g (0.5 mole) of sodium dichromate. The resulting mixture was stirred for 2 hours at room temperature and then heated on a steam bath for 4 hours, then cooled, after which the reaction mixture was poured into 9 liters of water. The solid was filtered off and recrystallized from benzene to give the desired product. M.P. 226°–228°C.

EXAMPLE 8

2,7-BIS(2-BROMOACETYL)XANTHEN-9-ONE

To a boiling mixture of 178.7 g (0.8 mole) cupric bromide in 500 ml. of ethyl acetate was added a boiling solution of 56.1 g (0.2 mole) of 2,7diacetylxanthen-9-one in 2 liters of chloroform. The resulting mixture was stirred and refluxed for 6 hours, then filtered while hot. The filtrate was evaporated to 500 ml. and cooled. The solid was filtered off and recrystallized from butanone to yield the desired product. M.P. 209°–210°C.

EXAMPLE 9

Following the procedure of Example 1, only substituting for 4-chlorobutyryl chloride, the appropriate molar equivalent amounts of 4-chlorovaleryl chloride or 4-chloro-2-methylbutyryl chloride which can be prepared by treating respectively γ-valerolactone and α-methyl-γ-butyrolactone with thionyl chloride and anhydrous zinc chloride [O. Wheeler and E. de Rodriguez, J. Org. Chem. 29, 1227 (1964)] the following compounds are prepared:
2,7-Bis(4-chlorovaleryl)xanthene
2,7-Bis(4-chloro-2-methylbutyryl)xanthene.

EXAMPLE 10

2,7-BIS(4-PIPERIDINOBUTYRYL)XANTHENE

A mixture of 19.6 g (0.05 mole) of 2,7-bis(4-chlorobutyryl)-xanthene, 34.0 g (0.4 mole) of piperidine, 16.6 g (0.1 mole) of potassium iodide and 200 ml. of butanone was refluxed with stirring for 2½ days. The reaction mixture was poured into 1000 ml. of water, and the solid which precipitated was filtered and recrystallized from methylene chloride-acetone then from acetone to give the desired product. M.P. 115°–117°C.

EXAMPLE 11

2,7-BIS(2-DIETHYLAMINOACETYL)XANTHENE DIHYDROCHLORIDE

To a solution of 200 ml. of diethylamine in 500 ml. of tetrahydrofuran were added 33.5 g (0.10 mole) of 2,7-bis(2-chloroacetyl)xanthene and 2 g of potassium iodide with warming. The reaction mixture was allowed to stand for 7 days then filtered and the filtrate was concentrated. The residual concentrate was dissolved in tetrahydrofuran, filtered, and the filtrate acidified with ethereal HCl to Congo Red. The resulting precipitate was filtered, recrystallized from diethyl ether, ethanol, and butanone and dried in vacuo to give the desired product. M.P. 164°–167°C. (dec.).

EXAMPLE 12

2,7-BIS(PIPERIDINOACETYL)XANTHENE DIHYDROCHLORIDE

To a solution of 200 ml. of piperidone in 500 ml. of tetrahydrofuran were added 33.5 g (0.1 mole) of 2,7-bis(2-chloroacetyl)xanthene and 2 g of potassium iodide with warming. The reaction mixture was allowed to stand for 7 days, filtered and the filtrate evaporated to dryness, leaving a residue which was treated with dilute acid and filtered. The filtrate was made alkaline, and the resulting oily product was extracted with methylene chloride. The methylene chloride solution was acidified with ethereal HCl which gave an oily product that was recrystallized from methanol-diethyl ether then vacuum dried to give the desired product. M.P. 260°–262°C.

EXAMPLE 13

2,7-BIS[3-(DIETHYLAMINO)PROPIONYL]XANTHENE DIHYDROCHLORIDE HYDRATE

A mixture of 18.2 g (0.05 mole) of 2,7-bis(3-chloropropionyl)xanthene, 2 g of potassium iodide, 100 ml. of diethylamine and 100 ml. of tetrahydrofuran was allowed to stand for 3 days then filtered. The filtrate was evaporated to dryness leaving a residue which was treated with 10% HCl and filtered. The filtrate was made alkaline, extracted with methylene chloride and treated with ethereal HCl. The resulting precipitate was filtered, recrystallized from methanol-diethyl ether and hydrated in a constant humidity chamber to give the desired product. M.P. 184.5°–185.5°C.

EXAMPLE 14

2,7-BIS[4-(DIETHYLAMINO)BUTYRYL]XANTHENE

A mixture of 31.3 g (0.08 mole) of 2,7-bis(4-chlorobutyryl)-xanthene, 2 g of potassium iodide and 90 ml. of diethyamine were placed in a bomb and heated on a steam bath for 24 hours. After cooling, the contents were poured into 300 ml. of water, and the resulting precipitate was extracted with methylene chloride and acidified with ethereal HCl to Congo Red to give the dihydrochloride salt of the desired product. The dihydrochloride salt was dissolved in water, filtered and the filtrate made alkaline with 20% NaOh solution. The resulting product was filtered, chromatographed on alumina using hexane as the eluant, recrystallized from heptane and dried in vacuo to give the desired product. M.P. 63°–65°C.

EXAMPLE 15

2,7-BIS[2-(DIMETHYLAMINO)ACETYL]XANTHENE DIHYDROCHLORIDE

To an ice cold mixture of 33.5 g (0.1 mole) 2,7-Bis(2-chloroacetyl)xanthene, 2 g of potassium iodide in 150 ml. of tetrahydrofuran in a Paar bomb was added an ice cold solution of dimethylamine and 150 ml. of tetrahydrofuran. The resulting mixture was warmed to room temperature and stirred for 7 days, filtered and the filtrate evaporated to dryness. The residue was dissolved in 10% HCl, filtered and the filtrate was made alkaline. The resulting solid was extracted with methylene chloride, acidified with ethereal HCl to Congo Red, filtered, recrystallized twice from methanol-diethyl ether, and dried to give the desired product. M.P. > 350°C.

EXAMPLE 16

2,7-BIS(4-MORPHOLINOBUTYRYL)XANTHENE

A mixture of 43.2 g (0.08 mole) 2,7-bis(4-chloro-1,1-diethoxybutyl)xanthene, 2 g. of potassium iodide, 100 ml. of morpholine and 100 ml. tetrahydrofuran was heated for 24 hours with stirring in a Paar bomb at 110°C. After cooling, the mixture was filtered and the filtrate was evaporated to dryness. The residue was cooled, dissolved in 300 ml. of 10% HCl and refluxed for 1 hour. The solution was cooled, filtered, the filtrate made alkaline, and extracted with chloroform. The chloroform extract was evaporated to dryness and the residue was recrystallized twice from a 1:4 mixture of benzene in heptane. Upon drying under vacuum, the desired product was obtained. M.P. 110°–111.5°C.

EXAMPLE 17

2,7-BIS[5-(DIALLYLAMINO)VALERYL]XANTHENE

A mixture of 41.9 g (0.1 mole) of 2,7-bis(5-chlorovaleryl)-xanthene, 2 g of potassium iodide, 100 ml of diallylamine and 200 ml. of tetrahydrofuran was heated and stirred at 120°C. for 24 hours. After cooling, the reaction mixture was filtered and the filtrate evaporated to dryness. The resulting residue was cooled, dissolved in 10% HCl, extracted with diethyl ether and made alkaline. The product was extracted with methylene chloride, evaporated to dryness, recrystallized six times from heptane and dried in vacuo to give the desired product. M.P. 54°–55°C.

EXAMPLE 18

2,7-BIS[2-(N-METHYLCYCLOHEXYLAMINO)ACETYL]XANTHENE DIHYDROCHLORIDE HYDRATE

A mixture of 33.5 g (0.1 mole) of 2,7-bis(2-chloroacetyl)-xanthene, 2 g of potassium iodide, 50.6 g (0.5 mole) of N-methylcyclohexylamine and 500 ml. of tetrahydrofuran was allowed to stand for seven days at room temperature, then filtered. The filtrate was evaporated to dryness, and the residue was cooled, then dissolved in 5% HCl and filtered. The filtrate was made alkaline and the product was extracted with methylene chloride, evaporated to a small volume, cooled, and acidified with ethereal HCl to Congo Red. The solid was filtered off and recrystallized four times from methanol-diethyl ether. After drying in vacuo and hydrating in a constant humidity chamber, the desired product was obtained. M.P. 203°–206°C.

EXAMPLE 19

2,7-BIS[5-(DIMETHYLAMINO)VALERYL]XANTHANE

A mixture of 20 g (0.048 mole) of 2,7-bis(5-chlorovaleryl)-xanthene, 2 g of potassium iodide, 200 ml. of 40% aqueous dimethylamine and 100 ml. of tetrahydrofuran was heated and stirred at 100°C. for 72 hours. After cooling, the excess dimethylamine and tetrahydrofuran were evaporated off. Upon cooling, a precipitate was filtered off and recrystallized twice from heptane and dried to give the desired product. M.P. 126.5°–128.5°C.

EXAMPLE 20

2,7-BIS(2-MORPHOLINOACETYL)XANTHENE DIHYDROCHLORIDE HYDRATE

A mixture of 22.7 g (0.068 mole) of 2,7-bis(-chloroacetyl)-xanthene, 2 g of potassium iodide, 200 ml. of morpholine and 500 ml. of tetrahydrofuran was allowed to stand for 7 days at room temperature, then filtered. The filtrate was evaporated to dryness and the resulting residue was cooled, dissolved in dilute HCl and filtered. The filtrate was made alkaline and the product was extracted with methylene chloride. The methylene chloride extract was evaporated to a small volume, cooled and acidified to Congo Red with ethereal HCl. The precipitate was filtered off and recrystallized three times from methanoldiethyl ether. After drying in vacuo and hydrating in a constant humidity chamber, the desired product was obtained. M.P. > 350°C.

EXAMPLE 21

Following the procedure of Example 10 only substituting for 2,7-bis(4-chlorobutyryl)xanthene the appropriate molar equivalent amounts of 2,7-bis(4-chlorovaleryl)xanthene or 2,7-bis(4-chloro-2-methylbutyryl)xanthene, the following compounds are prepared:
2,7-Bis(4-piperidinovaleryl)xanthene
2,7-Bis(4-piperidino-2-methylbutyryl)xanthene.

EXAMPLE 22

Following the procedure of Example 10, only substituting for piperidine, the appropriate molar equivalent amounts of N-methylpiperazine, 4-methylpiperidine, 4-propylpiperidine or pyrrolidine, the following compounds are prepared:
2,7-Bis[4-(4-methyl-1-piperazinyl)butyryl]xanthene,
2,7-Bis[4-(4-methylpiperidino)butyryl]xanthene,
2,7-Bis[4-(4-propylpiperidino)butyryl]xanthene,
2,7-Bis(4-pyrrolidinobutyryl)xanthene.

EXAMPLE 23

2,7-BIS(5-PIPERIDINOVALERYL)XANTHENE

A mixture of 30 g. (0.07 mole) of 2,7-bis(5-chlorovaleryl)-xanthene, 2 g of potassium iodide, 100 ml. of piperidine, and 200 ml. of tetrahydrofuran was heated and stirred at 100°C. for 24 hours. After cooling, the tetrahydrofuran was evaporated off and the resulting mixture was poured into water. The resulting solid was filtered off and recrystallized twice from heptane to give the desired product after drying at 80°C. under vacuum. M.P. 129°–130°C.

EXAMPLE 24

2,7-BIS(2-DIETHYLAMINOACETYL)XANTHEN-9-ONE

To a mixture of 2,7-bis(2-bromoacetyl)xanthen-9-one in tetrahydrofuran is added diethylamine, each cooled to −20°C. The reaction mixture is maintained at −20°C. for 24 hours then allowed to warm slowly to room temperature and then maintained at room temperature for 5 days. The mixture is filtered, and the filtrate evaporated to dryness. The resulting residue is dissolved in dilute HCl, filtered and the filtrate is made alkaline, keeping the temperature of the mixture around 0°C. The mixture is extracted with methylene chloride, and the extract acidified to Congo Red. The resulting solid is filtered off and recrystallized from methanol-diethylether to give the desired product.

EXAMPLE 25

2,7-BIS(4-PIPERIDINOBUTYRYL)XANTHEN-9-ONE

To a solution of 9.8 g (0.025 mole) of 2,7-bis(4-piperidinobutyryl)xanthene in 300 ml. of glacial acetic acid was added 9.8 g (0.033 mole) of sodium dichromate over ½ hour. The mixture was stirred for 1½ hours, refluxed for 1 hour, then evaporated to near dryness, cooled, diluted with water and made alkaline with 28% NH₄OH solution. The resulting solid was extracted with methylene chloride, chromatographed on alumina using methylene chloride as the eluant, recrystallized from heptane and dried under vacuum at 60°C. to give the desired product. M.P. 93°–95°C.

EXAMPLE 26

2,7-BIS(5-PIPERIDINOVALERYL)XANTHEN-9-ONE

Following the procedure of Example 25, only substituting for 2,7-bis(4-piperidinobutyryl)xanthene, 25.8 g (0.05 mole) 2,7-bis(5-piperidinovaleryl)xanthene and using 600 ml. of glacial acetic acid and 19.7 g (0.066 mole) sodium dichromate, the solid obtained was recrystalllized from a benzene-heptane mixture to give the desired product. M.P. 109°–110°C.

EXAMPLE 27

4,5-BIS(4-DIMETHYLAMINOBUTYRYL)XANTHENE

A. 9-Oxoxanthene-4,5-dicarboxylic acid which is prepared by potassium permanganate oxidation of the corresponding 4,5-dimethylxanthen-9-one [M. Schopff, Ber. 25, 3647 (1892)]49 is reduced to xanthene-4,5-dicarboxylic acid by a Wolff-Kishner reduction (N. Ishikawa, Yuki Gose: Kagaku Kyokai Shi 17, 553–6 (1959); CA 54:450]. The xanthene dicarboxylic acid derivative is converted to xanthene-4,5-dipiperidide by conventional procedures.

B. To a cooled solution of 3-(dimethylamino)propyl magnesium chloride, prepared from 12.1 g (0.5 mole) of magnesium and 60.8 g (0.50 mole) of 3-(dimethylamino)propyl chloride in 500 ml. of tetrahydrofuran, is added dropwise 23.6 g (0.1 mole) of xanthene-4,5-dipiperidide. The reaction mixture is warmed slowly to room temperature and stirred for 24 hours. The Grignard complex is decomposed by treating the reaction mixture with a solution of ammonium chloride, and the product is isolated.

EXAMPLE 28

3,6-BIS(4-DIMETHYLAMINOBUTYRYL)XANTHENE

Following the procedure of Example 27A, xanthene-3,6-dipiperidide is prepared from 3,6-dimethylxanthene-9-one [O. Weber, Ber. 25, 1745 (1892)].

Following the procedure of Example 27B, only substituting for xanthene-4,5-dipiperidide, the appropriate molar equivalent amount of xanthene 3,6-dipiperidide, the desired product is obtained.

EXAMPLE 29

2,6-BIS(4-DIMETHYLAMINOBUTYRYL)XANTHENE

Xanthene-2,6-dicarboxylic acid, which is prepared by a Wolff-Kishner reduction of 9-oxoxanthene-3-carboxylic acid (A. Goldberg and A. Wragg, J. Chem. Society, 1958, 4277) followed by a Friedel Crafts reaction with oxalyl chloride, is converted to xanthene-2,6-dipiperidide by conventional procedures.

Following the procedure of Example 27B, only substituting for xanthene-4,5-dipiperidide the appropriate molar equivalent amount of xanthene-2,6-dipiperidide, the desired product is obtained.

EXAMPLE 30

2,7-BIS-(3-DIETHYLAMINOPROPIONYL)XANTHENE DIHYDROCHLORIDE HYDRATE

A mixture of 12.7 g. (0.0477 mole) of 2,7-diacetylxanthene (Ng. D. Xuong and Ng, Ph. Buu-Hoi, J. Chem. Soc. 1952, 3741), 10.8 g. (0.0985 mole) of diethylamine hydrochloride, 4.7 g. (0.156 mole) of para-formaldehyde and 50 ml. of isoamyl alcohol is stirred and refluxed for 15 minutes. The reaction mixture is cooled, treated with anhydrous ether, and the resulting solid filtered and recrystallized from chloroform-ethyl acetate and methanol-anhydrous ether to give the desired product.

EXAMPLE 31

2,7-BIS(4-AMINOBUTYRYL)XANTHENE DIHYDROCHLORIDE 2,7-Bis(4-phthalimidobutyryl)xanthene, prepared from 4-phthalimidobutyryl chloride and xanthene by the method of S. S. Cheng et al., J. Med. Chem. 9, 945 (1966), is treated with 700 ml. of hot glacial acetic acid after which 200 ml. of concentrated hydrochloric acid is added gradually with stirring. The mixture is heated to reflux for 24 hours with a constant stream of HCl gas passing through the mixture The reaction mixture is stirred and refluxed for an additional 24 hours, cooled, and the product worked up in the usual manner.

EXAMPLE 32

An illustrative composition for a parenteral injection is the following wherein the quantities are on a weight to volume basis.

| | | |
|---|---|---|
| (a) | 2,7-bis[2-(dimethylamino)acetyl]xanthene dihydrochloride | 100 mg. |
| (b) | Sodium chloride | q.s. |
| (c) | Water for injection to make | 10 ml. |

The composition is prepared by dissolving the active ingredient and sufficient sodium chloride in water for injection to render the solution isotonic. The composition may be dispensed in a single ampule containing 100 mg. of the active ingredient for multiple dosage or in 10 ampules for a single dosage.

EXAMPLE 33

An illustrative composition for hard gelatin capsules is as follows:

| | | Per Capsule |
|---|---|---|
| (a) | 2,7-bis[2-(dimethylamino)acetyl]xanthene dihydrochloride | 200 mg. |
| (b) | Talc | 35 mg. |

The formulation is prepared by passing the dry powders of (a) and (b) through a fine mesh screen and mixing them well. The powder is then filled into No. 0 hard gelatin capsules at a net fill of 235 mg. per capsule.

EXAMPLE 34

An illustrative composition for tablets is as follows:

| | | Per Tablet |
|---|---|---|
| (a) | 2,7-bis[2-(dimethylamino)acetyl]xanthene dihydrochloride | 100 mg. |
| (b) | Wheat starch | 15 mg. |
| (c) | Lactose | 33.5 mg. |
| (d) | Magnesium stearate | 1.5 mg. |

Preparation:

A granulation obtained upon mixing lactose with the starch and granulated starch paste is dried, screened and mixed with the active ingredient and magnesium stearate. The mixture is compressed in tablets weighing 150 mg. each.

EXAMPLE 35

An illustrative composition for pills is as follows:

| | | Per Pill |
|---|---|---|
| (a) | 2,7-bis[2-(dimethylamino)acetyl]xanthene dihydrochloride | 100 mg. |
| (b) | Starch, corn | 90 mg. |
| (c) | Liquid glucose | 10 mg. |

The pills are prepared by blending the active ingredient and starch and then adding the liquid glucose with thorough kneading to form a plastic mass. The pills are then cut and formed from the plastic pill mass.

EXAMPLE 36

A 2% weight per volume syrup of 2,7-bis[2-(dimethylamino)acetyl]xanthene dihydrochloride can be prepared by the usual pharmaceutical techniques according to the following formula:

| | | Grams |
|---|---|---|
| (a) | Finely divided 2,7-bis[2-(dimethylamino)acetyl]xanthene dihydrochloride | 2.0 |
| (b) | Sucrose | 33.3 |
| (c) | Chloroform | 0.25 |
| (d) | Sodium benzoate | 0.4 |
| (e) | Methyl p-hydroxybenzoate | 0.02 |
| (f) | Vanillin | 0.04 |
| (g) | Glycerol | 1.5 |
| (h) | Purified water to 100.0 ml. | |

EXAMPLE 37

2,7-Bis[2-(dimethylamino)acetyl]xanthene dihydrochloride is mixed with soybean meal to prepare an animal feed concentrate containing 10 grams of said xanthene compound per pound of the medicated feed. This can subsequently be diluted with a mixed grain ration to give a medicated feed containing 50 milligrams of the xanthene per pound of the medicated feed.

EXAMPLE 38

The following formulation is illustrative of a dusting powder:

| | Per Kilogram |
|---|---|
| (a) 2,7-bis[2-(dimethylamino)acetyl]xanthene dihydrochloride | 20 grams |
| (b) Silica aerogel | 980 grams |

The dusting powder is prepared by intimately admixing the ingredients. The mixture is then packaged in dispensing containers.

EXAMPLE 39

An illustrative composition for a parenteral injection is the following aqueous emulsion.

| Each ml. contains | Ingredient | Amount |
|---|---|---|
| 50 mg | 2,7-bis[2-(dimethylamino)acetyl]-xanthene dihydrochloride | 1.000 g. |
| 100 mg. | Polyoxyethylene sorbitan monooleate | 2.000 g. |
| 0.0064 gm. | Sodium chloride | 0.128 g. |
| | Water for injecton, q.s. | 20.000 ml. |

The composition of Example 39 is prepared by dissolving 0.64 g. of sodium chloride in 100 ml. of water for injection; mixing the polyoxyethylene sorbitan monooleate with the xanthene, adding a sufficient solution of the sodium chloride in water to the active ingredient and polyoxyethylene sorbitan monooleate to make 20 ml; shaking the mixture; and then autoclaving it for 20 minutes at 110°C. at 15 p.s.i.g. steam pressure. The composition can be dispensed in a single ampule for multiple dosage or in 10 or 20 ampules for single dosages.

Examples 40 to 62 illustrate in vivo or in vitro antiviral studies with active ingredients of this invention. Each example recites pertinent information involved. Table 1 lists the active ingredient which was administered in each of the examples. Although it is believed that the headings in the examples are self-explanatory, some of the headings are explained as follows: The "Challenge", that is, inoculation with a virus, used is generally fatal to all the untreated, that is, control, animals in the experiment. "Time of death" refers to the average time of death for the untreated animals. The "Treatment" was prophylactic or therapeutic or both. The term "volume" refers to the volume of composition administered per dose which contained the active ingredient dissolved in sterile water which also contained 0.15 percent of hydroxyethylcellulose. The control animals received a sham dosage of the same volume of the vehicle which did not contain the active ingredient. The abbreviation "STR" is survival time ratio, which is calculated by dividing the mean day of death of the control animals into the mean day of death of the treated animals during the period of observation. The activity of the compound in the example involved is further characterized, for example, low, medium, high, and the like. A survival time ratio (STR) of less than 0.90 indicates that the compound was toxic a ratio of 0.90 to that there is no activity; a ratio of 1.10 to 1.19 indicates low or weak activity; a ratio of 1.20 to 1.29 indicates medium activity; and a ratio of 1.30 and greater indicates high activity.

Table 1

| Example No. | Active Ingredient |
|---|---|
| 40 & 41 | 2,7-bis(4-piperidinobutyryl)xanthene |
| 42 & 43 | 2,7-bis[4-(diethylamino)butyryl]xanthene |
| 44 & 45 | 2,7-bis(2-diethylaminoacetyl)xanthene dihydrochloride |
| 46 | 2,7-bis[5-(dimethylamino)valeryl]xanthene |
| 47 | 2,7-bis(5-piperidinovaleryl)xanthene |
| 48 & 49 | 2,7-bis(4-piperidinobutyryl)xanthen-9-one |
| 50 & 51 | 2,7-bis(piperidinoacetyl)xanthene dihydrochloride |
| 52 | 2,7-bis(5-piperidinovaleryl)xanthen-9-one |
| 53 & 54 | 2,7-bis[3-(diethylamino)propionyl]xanthene dihydrochloride hydrate |
| 55 | 2,7-bis(4-morpholinobutyryl)xanthene |
| 56 & 57 | 2,7-bis[2-(dimethylamino)acetyl]xanthene dihydrochloride |
| 58 & 59 | 2,7-bis(2-morpholinoacetyl)xanthene dihydrochloride hydrate |
| 60 & 61 | 2,7-bis[2-(N-methylcyclohexylamino)acetyl]xanthene dihydrochloride hydrate |
| 62 | 2,7-bis[5-(diallylamino)valeryl]xanthene |

| Example No. | 40 | 41 | 42 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 13 $LD_{50}$ | 13 $LD_{50}$ | 12 $LD_{50}$ |
| route | Subcutaneous | Subcutaneous | Subcutaneous |
| time of death | 4.2 days | 4.2 days | 5.0 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 10 |
| No. in control group | 20 | 20 | 20 |
| TREATMENT | Prophylactic and Therapeutic | Prophylactic and Therapeutic | Prophylactic Therapeutic |
| dosage level | 50 mg/kg | 50 mg/kg | 50 mg/kg |
| route | Subcutaneous | Oral | Subcutaneous |
| volume | 0.25 ml. | 0.25 ml. | 0.25 ml. |
| time pre-challenge | 28, 22, 2 hours | 28, 22, 2 hours | 28, 22, 2 hours |
| post-challenge | 2, 20, 26 hours | 2, 20, 26 hours | 2 hours |
| RESULTS | | | |
| STR | 1.33 | 1.20 | 1.40 |
| activity | high | medium | high |

| Example No. | 43 | 44 | 45 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 12 $LD_{50}$ | 7 $LD_{50}$ | 7 $LD_{50}$ |
| route | Subcutaneous | Subcutaneous | Subcutaneous |
| time of death | 5.0 days | 4.3 days | 4.3 days |
| period of observation | 9 days | 9 days | 9 days |
| ANIMAL | Mice | Mice | Mice |
| weight | 12–15 grams | 12–15 grams | 12–15 grams |

| Example No. | 43 | 44 | 45 |
|---|---|---|---|
| No. in treated group | 10 | 10 | 10 |
| No. in control group | 20 | 20 | 20 |
| TREATMENT | Prophylactic and Therapeutic | Prophylactic and Therapeutic | Prophylactic |
| dosage level | 50 mg/kg | 50 mg/kg | 250 mg/kg |
| route | Oral | Subcutaneous | Oral |
| volume | 0.25 ml. | 0.25 ml. | 0.25 ml. |
| time pre-challenge | 28, 22, 2 hours | 28, 22, 2 hours | 22 hours |
| post-challenge | 2 hours | 2 hours | None |
| RESULTS | | | |
| STR | 1.36 | 1.37 | 2.16 |
| activity | high | high | high |

| Example No. | 46 | 47 | 48 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 8 $LD_{50}$ | 10 $LD_{50}$ | 45 $LD_{50}$ |
| route | Subcutaneous | Subcutaneous | Subcutaneous |
| time of death | 4.4 days | 4.6 days | 4.2 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 10 |
| No. in control group | 20 | 20 | 20 |
| TREATMENT | Prophylactic | Prophylactic and Therapeutic | Prophylactic and Therapeutic |
| dosage level | 50 mg/kg | 50 mg/kg | 50 mg/kg |
| route | Subcutaneous | Subcutaneous | Subcutaneous |
| volume | 0.25 ml. | 0.25 ml. | 0.25 ml. |
| time pre-challenge | 28, 22, 2 hours | 28, 22, 2 hours | 28, 22, 2 hours |
| post-challenge | None | 2 hours | 2 hours |
| RESULTS | | | |
| STR | 1.59 | 2.28 | 1.50 |
| activity | high | high | high |

| Example No. | 49 | 50 | 51 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 45 $LD_{50}$ | 12 $LD_{50}$ | 12 $LD_{50}$ |
| route | Subcutaneous | Subcutaneous | Subcutaneous |
| time of death | 4.2 days | 5.1 days | 5.1 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 10 |
| No. in control group | 20 | 20 | 20 |
| TREATMENT | Prophylactic | Prophylactic and Therapeutic | Prophylactic and Therapeutic |
| dosage level | 250 mg/kg | 50 mg/kg | 50 mg/kg |
| route | Oral | Subcutaneous | Oral |
| volume | 0.25 ml. | 0.25 ml. | 0.25 ml. |
| time pre-challenge | 22 hours | 28, 22, 2 hours | 28, 22, 2 hours |
| post-challenge | None | 2 hours | 2 hours |
| RESULTS | | | |
| STR | 1.50 | 1.37 | 1.22 |
| activity | High | High | medium |

| Example No. | 52 | 53 | 54 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 27 $LD_{50}$ | 28 $LD_{50}$ | 28 $LD_{50}$ |
| route | Subcutaneous | Subcutaneous | Subcutaneous |
| time of death | 4.3 days | 4.2 days | 4.2 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 9 |
| No. in control group | 20 | 20 | 20 |
| TREATMENT | Prophylactic and Therapeutic | Prophylactic and Therapeutic | Prophylactic and Therapeutic |
| dosage level | 50 mg/kg | 50 mg/kg | 250 mg/kg |
| route | Subcutaneous | Subcutaneous | Oral |
| volume | 0.25 ml. | 0.25 ml. | 0.25 ml. |
| time pre-challenge | 28, 22, 2 hours | 28, 22, 2 hours | 22 hours |
| post-challenge | 2 hours | 2 hours | None |
| RESULTS | | | |
| STR | 1.56 | 1.114 | 1.17 |
| activity | high | weak | weak |

| Example No. | 55 | 56 | 57 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 8 $LD_{50}$ | 6 $LD_{50}$ | 6 $LD_{50}$ |
| route | Subcutaneous | Subcutaneous | Subcutaneous |
| time of death | 4.6 days | 4.6 days | 4.6 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 10 |

-continued

| Example No. | 55 | 56 | 57 |
|---|---|---|---|
| No. in control group | 20 | 20 | 20 |
| TREATMENT | Prophylactic and Therapeutic | Prophylactic and Therapeutic | Prophylactic and Therapeutic |
| dosage level | 50 mg/kg | 50 mg/kg | 50 mg/kg |
| route | Subcutaneous | Subcutaneous | Oral |
| volume | 0.25 ml. | 0.25 ml. | 0.25 ml. |
| time pre-challenge | 28, 22, 2 hours | 28, 22, 2 hours | 28, 22, 2 hours |
| post-challenge | 2 hours | 2 hours | 2 hours |
| RESULTS | | | |
| STR | 1.33 | 2.02 | 1.76 |
| activity | high | high | high |

| Example No. | 58 | 59 | 60 |
|---|---|---|---|
| VIRUS | Encephalomyocarditis | Encephalomyocarditis | Encephalomyocarditis |
| type | RNA; Picornavirus | RNA; Picornavirus | RNA; Picornavirus |
| challenge | 6 $LD_{50}$ | 6 $LD_{50}$ | 6 $LD_{50}$ |
| route | Subcutaneous | Subcutaneous | Subcutaneous |
| time of death | 4.6 days | 4.6 days | 4.6 days |
| period of observation | 9 days | 9 days | 9 days |
| ANIMAL | Mice | Mice | Mice |
| weight | 12–15 grams | 12–15 grams | 12–15 grams |
| No. in treated group | 10 | 10 | 10 |
| No. in control group | 20 | 20 | 20 |
| TREATMENT | Prophylactic and Therapeutic | Prophylactic and Therapeutic | Prophylactic and Therapeutic |
| dosage level | 50 mg/kg | 50 mg/kg | 50 mg/kg |
| route | Subcutaneous | Oral | Subcutaneous |
| volume | 0.25 ml. | 0.25 ml. | 0.25 ml. |
| time pre-challenge | 28, 22, 2 hours | 28, 22, 2 hours | 28, 22, 2 hours |
| post-challenge | 2 hours | 2 hours | 2 hours |
| RESULTS | | | |
| STR | 1.11 | 1.35 | 1.39 |
| activity | weak | high | high |

| Example No. | 61 | 62 |
|---|---|---|
| VIRUS | Encephalomyocarditis | Encephalomyocarditis |
| type | RNA; Picornavirus | RNA; Picornavirus |
| challenge | 6 $LD_{50}$ | 8 $LD_{50}$ |
| route | Subcutaneous | Subcutaneous |
| time of death | 4.6 days | 4.8 days |
| period of observation | 9 days | 9 days |
| ANIMAL | Mice | Mice |
| weight | 12–15 grams | 12–15 grams |
| No. in treated group | 10 | 10 |
| No. in control group | 20 | 20 |
| TREATMENT | Prophylactic and Therapeutic | Prophylactic and Therapeutic |
| dosage level | 50 mg/kg | 50 mg/kg |
| route | Oral | Subcutaneous |
| volume | 0.25 ml. | 0.25ml. |
| time pre-challenge | 28, 22, 2 hours | 28, 22, 2 hours |
| post-challenge | 2 hours | 2 hours |
| RESULTS | | |
| STR | 1.22 | 1.46 |
| activity | medium | high |

We claim:

1. A pharmaceutical compositon for inhibiting viral infections, in unit dosage form, comprising a significant quantity of a pharmaceutically acceptable carrier and from about 0.1 milligram to about 3 grams of a compound selected from a base of the formula

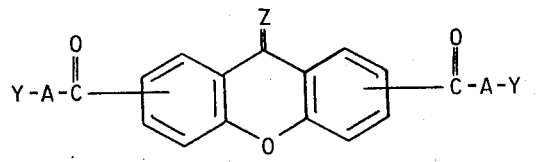

wherein Z is a member selected from the group consisting of oxygen of $H_2$; each A is a straight or branched alkylene chain of from 1 to about 6 carbon atoms; and each Y is a member selected from the group consisting of A. the group

wherein $R^1$ and $R^2$ are individually selected from the group consisting of hydrogen, lower alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group; or B. the group

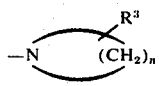

wherein $n$ is a whole integer from 4 to 6, and $R^3$ is a member selected from the group consisting of hydrogen or lower alkyl of from 1 to about 4 carbon atoms and can be linked to any one of the carbon atoms of the heterocyclic group; or C. the group

wherein X is a member selected from the group consisting of oxygen or NR$^4$, and R$^4$ is hydrogen or lower alkyl of from 1 to about 4 carbon atoms,
or a pharmaceutically acceptable acid addition salt thereof.

2. The composition of claim 1 wherein the compound has one of the

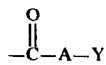

groups in the 2-position of the xanthene ring and the other such group is in the 7-position.

3. The composition of claim 2 wherein each Y of the compound is the group

4. The composition of claim 3 wherein the compound is 2,7-bis[4-(diethylamino)butyryl]xanthene or a pharmaceutically acceptable acid addition salt thereof.

5. The composition of claim 3 wherein the compound is 2,7-bis[2-(diethylamino)acetyl]xanthene or a pharmaceutically acceptable acid addition salt thereof.

6. The composition of claim 3 wherein the compound is 2,7-bis[2-(dimethylamino)acetyl]xanthene or a pharmaceutically acceptable acid addition salt thereof.

7. The composition of claim 2 wherein each Y of the compound is the group

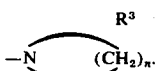

8. The composition of claim 7 wherein n in the compound is the integer 5.

9. The composition of claim 2 wherein each Y in the compound is the group

10. The composition of claim 9 wherein X in the compound is oxygen.

11. The composition of claim 1 wherein Z in the compound is H$_2$.

12. The composition of claim 11 wherein the compound has one of the

groups in the 2-position of the xanthene ring and the other such group is in the 7-position.

13. The composition of claim 1 wherein Z of the compound is oxygen.

14. The composition of claim 13 wherein the compound has

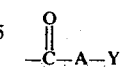

groups in the 2-position of the xanthene rings and the other such group is in the 7-position.

15. A method of preventing or inhibiting viral infections susceptible to replication inhibition by interferon induction which comprises administering to a warm-blooded host having cells susceptible to invasion by pathogenic viral agents, within an antivirally effective time period, an antivirally effective amount of a compound selected from a base of the formula

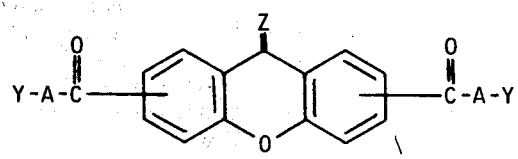

wherein Z is a member selected from the group consisting of oxygen or H$_2$; each A is a straight or branched alkylene chain of from 1 to about 6 carbon atoms; and each Y is a member selected from the group consisting of A. the group

wherein R$^1$ and R$^2$ are individually selected from the group consisting of hydrogen, lower alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group; or B. the group

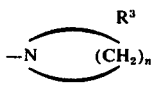

wherein n is a whole integer from 4 to 6, and R$^3$ is a member selected from the group consisting of hydrogen or lower alkyl of from 1 to about 4 carbon atoms and can be linked to any one of the carbon atoms of the heterocyclic group; or C. the group

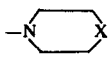

wherein X is a member selected from the group consisting of oxygen or NR$^4$, and R$^4$ is hydrogen or lower alkyl of from 1 to about 4 carbon atoms,
or a pharmaceutically acceptable acid addition salt thereof.

16. The method of claim 15 wherein the compound has one of the

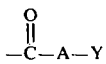

groups in the 2-position of the xanthene ring and the other such group is in the 7-position.

17. The method of claim 16 wherein each Y of the compound is the group

18. The method of claim 17 wherein the compound is 2,7-bis[4-(diethylamino)butyryl]xanthene or a pharmaceutically acceptable acid addition salt thereof.

19. The method of claim 17 wherein the compound is 2,7-bis[2-(diethylamino)acetyl]xanthene or a pharmaceutically acceptable acid addition salt thereof.

20. The method of claim 17 wherein the compound is 2,7-bis[2-(diethylamino)acetyl]xanthene or a pharmaceutically acceptable acid addition salt thereof.

21. The method of claim 16 wherein each Y of the compound is the group

22. The method of claim 21 wherein $n$ in the compound is the integer 5.

23. The method of claim 16 wherein each Y in the compound is the group

24. The method of claim 23 wherein X in the compound is oxygen.

25. The method of claim 15 wherein Z in the compound is $H_2$.

26. The method of claim 25 wherein the compound has one of the

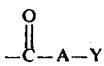

groups in the 2-position of the xanthene ring and the other such group is in the 7-position.

27. The method of claim 15 wherein Z of the compound is oxygen.

28. The method of claim 27 wherein the compound has one of the

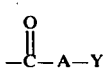

groups in the 2-position of the xanthene rings and the other such group is in the 7-position.

* * * * *

UNITED STATES PATENT AND TRADEMARK OFFICE
CERTIFICATE OF CORRECTION

PATENT NO. : 3,957,989
DATED : May 18, 1976
INVENTOR(S) : Robert W. Fleming, Arthur D. Sill and Francis W. Sweet It is certified that error appears in the above-identified patent and that said Letters Patent are hereby corrected as shown below:

Column 4, line 26, "mentiond" should read "mentioned". Column 5, lines 47, 52-53; column 6, line 5 and column 6, line 55, "inredient(s)" should read "ingredient(s)". Column 5, line 1 and column 13, line 65, "invenion" should read "invention"; line 53, "inhbitied" should read "inhibited". Column 6, line 11, "inerferon" should read "interferon"; line 57, "topicaly" should read "topically". Column 8, lines 9-10, "particularly" should read "parenterally"; line 32, "normally active" should read "normally liquid". Column 9, line 14, "catalysts" should read "catalysis". Column 16, line 33, "piperidone" should read "piperidine". Column 24, lines 20-21, "toxic a ratio of 0.90 to that there is no activity;" should read "toxic; a ratio of 0.90 to 1.09 indicates that there is no activity;". Column 29, claim 7, line 40; column 30, claim 15, line 45; and column 31, claim 21, line 30, .

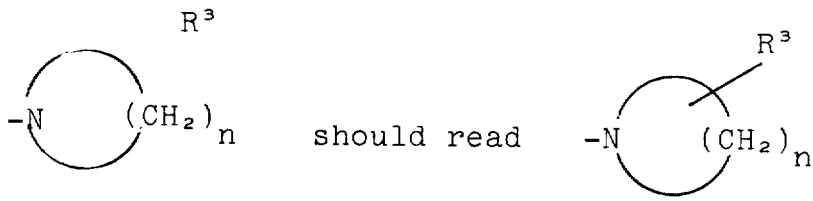

Signed and Sealed this twelfth Day of July 1977

[SEAL]

Attest:

RUTH C. MASON
Attesting Officer

C. MARSHALL DANN
Commissioner of Patents and Trademarks